(12) United States Patent
Morin et al.

(10) Patent No.: US 9,198,741 B2
(45) Date of Patent: Dec. 1, 2015

(54) ORTHODONTIC APPLIANCE HAVING SLIDING RODS

(75) Inventors: Jean-Charles Morin, Saint Aignan sur Cher (FR); Elie Callabe, Mont Pres Chambord (FR)

(73) Assignee: PUL CONCEPT, Noyers sur Cher (FR)

( * ) Notice: Subject to any disclaimer, the term of this patent is extended or adjusted under 35 U.S.C. 154(b) by 0 days.

(21) Appl. No.: 14/115,232

(22) PCT Filed: May 3, 2012

(86) PCT No.: PCT/IB2012/000851
§ 371 (c)(1),
(2), (4) Date: Nov. 1, 2013

(87) PCT Pub. No.: WO2012/150494
PCT Pub. Date: Nov. 8, 2012

(65) Prior Publication Data
US 2014/0072928 A1     Mar. 13, 2014

(30) Foreign Application Priority Data
May 3, 2011 (FR) ...................................... 11 01364

(51) Int. Cl.
*A61C 7/36* (2006.01)
(52) U.S. Cl.
CPC ........................................ *A61C 7/36* (2013.01)
(58) Field of Classification Search
CPC ....................................................... A61C 7/36
USPC ............................................... 433/18, 19, 21
See application file for complete search history.

(56) References Cited

U.S. PATENT DOCUMENTS

| 5,352,116 | A |   | 10/1994 | West |   |
|---|---|---|---|---|---|
| 5,738,514 | A | * | 4/1998 | DeVincenzo et al. | ........... 433/19 |
| 5,829,975 | A |   | 11/1998 | Gold |   |
| 5,879,157 | A | * | 3/1999 | Scheu | ....... A61C 7/36 433/19 |
| 6,012,920 | A | * | 1/2000 | Woo | ......... A61C 7/10 433/19 |
| 6,719,557 | B1 | * | 4/2004 | Williams | ............... A61C 7/36 433/18 |
| 2010/0190127 | A1 | * | 7/2010 | Ghantiwala et al. | ............ 433/18 |

FOREIGN PATENT DOCUMENTS

| DE | 203 15 857 U1 | 12/2003 |
| EP | 1 712 203 A1 | 10/2006 |
| FR | 2 813 783 A1 | 3/2002 |
| WO | WO 96/04864 A1 | 2/1996 |
| WO | WO 03/032859 A1 | 4/2003 |
| WO | WO 2007/081990 A2 | 7/2007 |

OTHER PUBLICATIONS

International Search Report issued in International Application No. PCT/IB2012/000851 mailed Aug. 6, 2012.

* cited by examiner

*Primary Examiner* — Edward Moran
(74) *Attorney, Agent, or Firm* — Oliff PLC

(57) ABSTRACT

An orthodontic appliance has sliding rods for the treatment of a lower jaw that is offset relative to the upper jaw. A sleeve is inserted between opposite ends of the tow rods, each of which being associated with one of the jaws. The second rod is screwed into the sleeve at one end, while the first rod is slidably mounted in the sleeve at the opposite end, with the adjustment of the position of the second rod relative to the sleeve being made by screwing and unscrewing.

9 Claims, 3 Drawing Sheets

ORTHODONTIC APPLIANCE HAVING SLIDING RODS

CROSS REFERENCE TO RELATED APPLICATIONS

This application is a national stage entry of PCT/IB2012/000851 filed May 3, 2012 and claims foreign priority to FR 1101364 filed May 3, 2011.

BACKGROUND OF THE INVENTION

The invention concerns the field of removable orthodontic appliances and, more particularly, appliances of this type having a sliding rod device between the jaws to realign the jaws in either direction.

The principle for treating temporomandibular joint dysfunction consists in using orthodontic appliances which posture the lower jaw (the mandible) forwards or backwards and are supported by the upper jaw (maxilla) in order to obtain stimulation of mandibular growth forwards or backwards respectively and a decrease in growth of the upper jaw forwards or backwards respectively. For this purpose, appliances are used comprising rods designed to slide one with respect to the other and forming a male/female assembly, with the rods being respectively attached to metal structures attached to resin occlusal splints fitted onto the teeth. Such an appliance having telescopic rods is described in particular in patent FR 2 813 783. In this case, the female rod is attached to the upper jaw and the male rod is attached to the mandible. The rods are designed to be inserted into each other and the length of insertion is sufficient for the male rod not to be dislodged during use. Before each insertion into the mouth, the rods must be reinserted into each other.

BRIEF SUMMARY OF THE INVENTION

The present invention is aimed at proposing an appliance to treat temporomandibular joint disorders which will provide effective treatment and user comfort while being particularly easy to insert and very inexpensive.

To this end, the invention proposes an appliance comprising a first rod fixed to a support designed to be associated with the lower jaw and a second rod fixed to a support designed to be associated with the upper jaw in which the rods are designed to move in relation to each other so that the jaws can move. A sleeve is placed between the rods in an assembly in which the second rod is screwed into the sleeve at one end, while the first rod is slidably mounted in the sleeve at the opposite end. The sleeve guides the first rod in its translational movement. The sleeve comprises spacing adjustment means to adjust the position of the second rod with respect to the sleeve and that of the first rod by screwing or unscrewing.

Thus, the invention advantageously places a part between the rods which, on the one hand, facilitates initial adjustment of jaw alignment by separating the lower rod from the upper rod by a distance which is determined by the requirements of the wearer of the appliance and, on the other hand, allows for sufficient play when the appliance is inserted between the jaws. It is particularly advantageous if it is the same part that enables the sliding rod to be guided and the other rod to be adjusted by screwing.

According to a characteristic of the invention, the sleeve is deformed at the end corresponding to the first rod when the rod is placed inside the sleeve in order to form a secure system designed to hold the first rod inside the sleeve. This ensures that the two rods do not separate and form an orthodontic appliance consisting of a sleeve and its associated supports combined in a single, easy-to-handle unit.

In its preferred embodiments, for the purpose described above, the sleeve of the appliance comprises an axial boring which extends from one end to the other and has three different diameters which divide the sleeve into three distinct functional portions, namely, an adjustment portion which corresponds to the boring with the smallest diameter and is designed to cooperate with the thread of the second rod; a guide portion which corresponds to the boring with the largest diameter and is designed for the first rod to slide inside; and a central portion of intermediate diameter which extends from the guide portion to the adjustment portion.

According to a secondary characteristic of the invention, the first rod has a collar/adapter whose diameter is approximately equal to the inside diameter of the guide portion of the sleeve, such that the collar guides the rod as it slides into the sleeve. In order to prevent the rod from sliding too far and going out the other side of the sleeve, the end of the sleeve is folded inwards towards the first rod when the collar is inside the sleeve, such that the collar and, by extension, the first rod assembly, is prevented from moving beyond the end of the sleeve when the collar is in contact with the end folded inwards.

According to another advantageous characteristic of the appliance according to the invention, a spring is inserted into the sleeve around the end of the first sliding rod, between the collar of the first rod and a shoulder formed inside the sleeve between the guide portion and the central portion of smaller dimension. The spring thus tends to return the said first rod into its initial position when it is displaced and compresses the spring. The fact that the spring is lodged in the sleeve means that the spring is forced to move axially due to the rigidity of the sleeve so that it is either in compression or pure decompression.

The spacing adjustment means of the appliance according to the invention comprises, at the very least, means to allow rotation of the sleeve and the resulting screwing or unscrewing of the sleeve with respect to the second rod. It also comprises means to block rotation so that a manual force must be applied to screw or unscrew the second rod.

The adjustment portion is split axially, forming lugs whose inside surface is threaded to take the second rod, the lugs being designed to press tightly against the second rod to prevent it from rotating. Radial holes are bored in a given circumference of the sleeve, spaced at regular angular intervals, the said holes being designed to take a key so that the sleeve can be rotated and thus screwed or unscrewed with respect to the second rod.

Thus, in order to adjust the jaw alignment before use, the practitioner adjusts the spacing of the rods with respect to each other by screwing or unscrewing the second rod into the sleeve, thus increasing or decreasing the space between the rods.

According to the different characteristics of the invention, starting at the end designed to cooperate with the sleeve and ending at the opposite end, the first rod consists of an approximately straight guide portion, then a collar that protrudes radially over the entire diameter of the rod and separates the guide portion from the rest of the rod, that is, successively, an approximately straight intermediate portion, with a smaller diameter than that of the collar but greater than that of the guide portion, and an attachment portion which extends the intermediate portion in an approximate C-shape with an elongated hole or eye, the attachment portion being designed to cooperate with the lower jaw support. Starting at the end designed to cooperate with the sleeve and ending at the opposite end, the second rod consists of a threaded end portion then an attachment portion, which extends the threaded portion in an approximate S-shape with an elongated hole or eye, the said attachment portion being designed to cooperate with the upper jaw support.

According to a characteristic of the invention, attachment of the rods to the corresponding supports is the same for both the upper jaw and the lower jaw. Each of the rods is thus attached by means of a pin passing through the eye in the attachment portion of the rod and through a tube welded to the support, the pin having a fine spindle designed to be inserted into the tube, at the end of which there is a ball which abuts against the edges of the eye.

Other characteristics and advantages of the invention will become more apparent during the following description illustrated by the figures below:

DETAILED DESCRIPTION OF THE DRAWINGS

Figure 1:
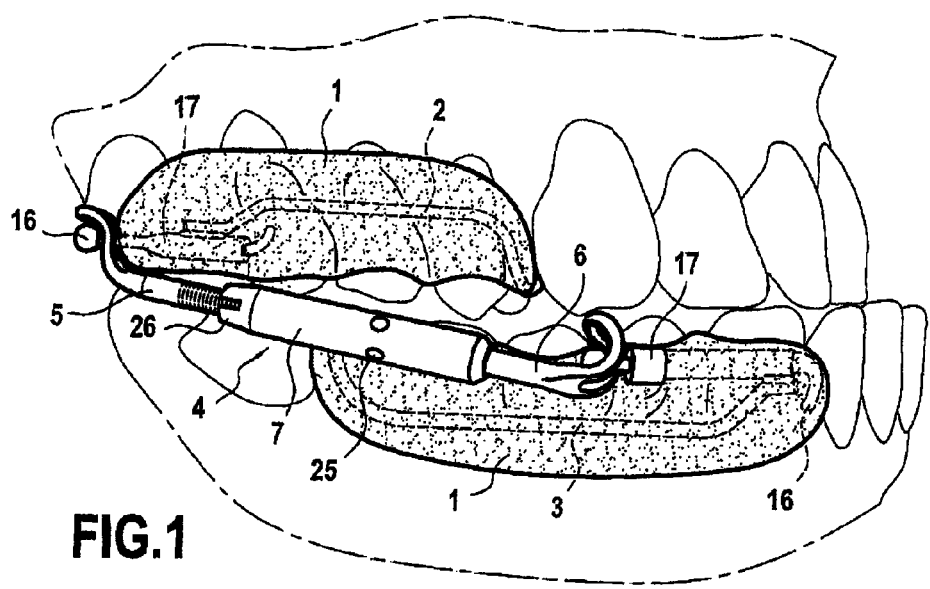
FIG. 1, which illustrates an orthodontic appliance according to the invention seen from the side, with the jaws closed.

According to the invention, and as illustrated in FIG. 1, an orthodontic appliance comprises a sliding device placed between the two jaws by means of a set of removable occlusal splints which guides the displacement of one jaw with respect to the other.

The removable occlusal splints 1 are made of resin with metal reinforcements embedded in each of the splints. An upper splint is thus placed over the teeth in the upper jaw, with an upper metal reinforcement 2 which is integral with the said upper splint, and a lower splint is placed symmetrically over the teeth of the lower jaw, with a lower metal reinforcement 3 which is integral with the said lower splint. An appliance having sliding rods 4 connects the two reinforcements in order to accompany and guide displacement of the jaws by means of splints fitted onto the teeth.

Figure 2:
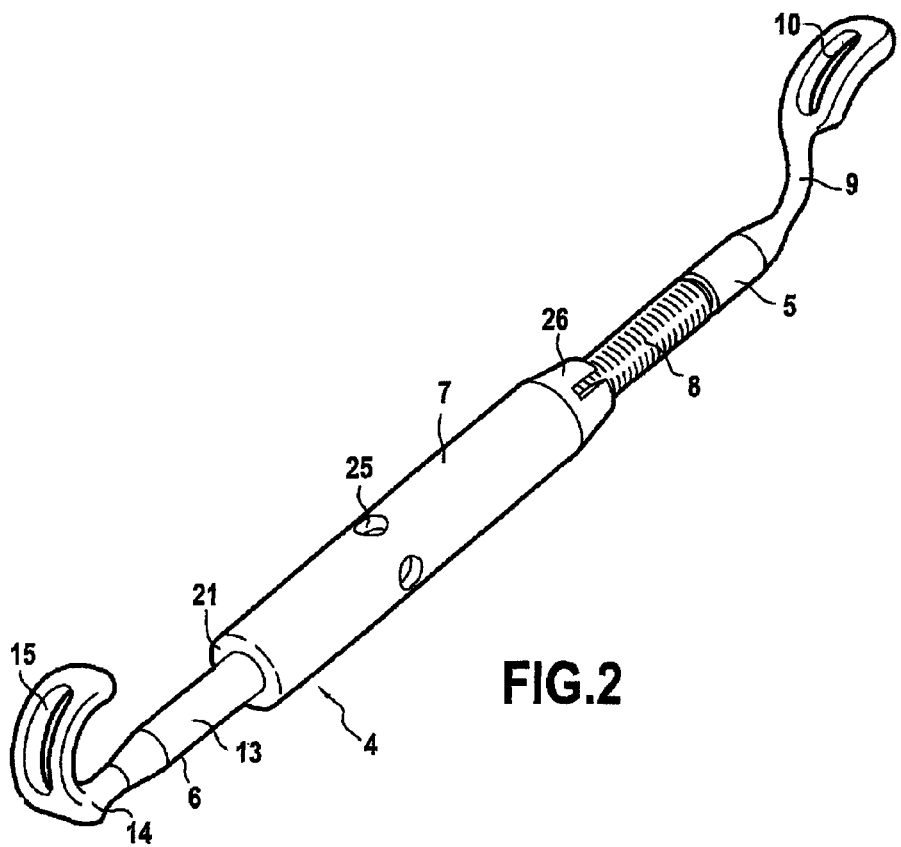
FIG. 2, which is a bird's eye view of the appliance having sliding rods as illustrated in FIG. 1, in which the sleeve is inserted between two rods, the first being partially screwed into the sleeve and the second being slidably mounted into the sleeve.
Figure 3:
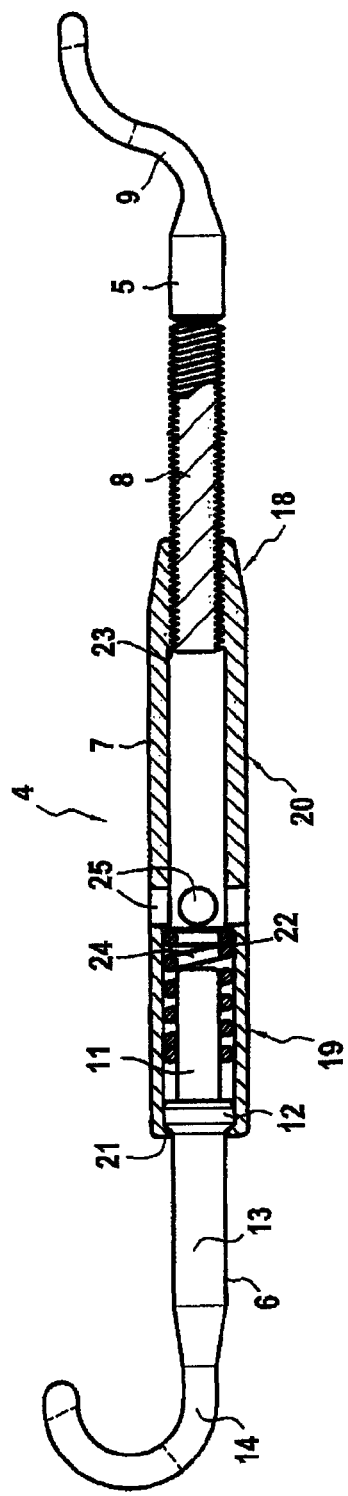
FIG. 3, which is an axial section of the appliance having sliding rods as illustrated in FIG. 2.
Figure 4:
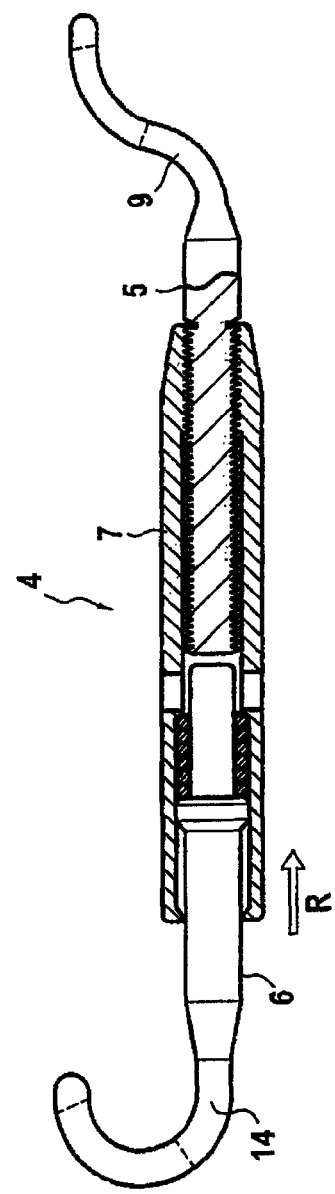
FIG. 4, which is a view similar to that of FIG. 3, but in which the appliance is in a different adjustment position, with the rod completely screwed in, and in a different functional position, with the sliding rod compressing the spring inside the sleeve.

The appliance, according to the first construction method represented in FIGS. 2 to 4, comprises an upper rod 5, a lower rod 6 and a sleeve 7. The sleeve is inserted between the two rods so that the opposite ends of the rods are inserted into the sleeve. Each rod is placed at one end of the sleeve, in its own functional portion.

As described above in more detail, the lower rod is slidably mounted on the end of the sleeve while the upper rod is screwed into the opposite end of the sleeve. Each rod thus comprises one end lodged in the sleeve and one end designed to be fixed to one of the occlusal splints and the corresponding metal reinforcement.

Starting at the end designed to cooperate with the sleeve and ending at the opposite end, the upper rod comprises a threaded end portion 8, followed by an attachment portion 9, which extends the threaded portion in an approximate S-shape which has an eye 10.

Starting at the end designed to cooperate with the sleeve and ending at the opposite end, the lower rod comprises an approximately straight guide portion 11, followed by a collar 12 that protrudes radially over the entire diameter of the rod and separates the guide portion from the rest of the rod, namely, an approximately straight intermediate portion 13, with a smaller diameter than that of the collar but greater than that of the guide portion, followed by an attachment portion 14 which extends the intermediate portion in an approximate C-shape which has an eye.

As can be seen in FIG. 1, the system used to attach the rods to the metal reinforcements is the same for both the upper reinforcement and the lower reinforcement.

The upper reinforcement and the upper rod are fixed by means of a pin 16 passing through the eye 10 and a tube 17 welded to the upper metal reinforcement. For this purpose, the pin 16 is equipped with a fine spindle designed to be inserted into the tube with a ball on the end that abuts against the edges of the eye.

When the pin is in position, that is, when the ball abuts against the edges of the eye and the spindle passes through the tube, the end of the pin opposite the ball is bent to keep the pin inside the tube and prevent the upper rod from moving with respect to the upper reinforcement and, by extension, with respect to the upper jaw when the appliance has been positioned inside the wearer's mouth.

Similarly, the lower rod is attached to the reinforcement of the lower splint by means of a pin 16 which is designed to cooperate with the eye 15 and a tube 17 welded to the lower metal reinforcement.

This results in a single unit consisting of an upper splint and a lower splint connected by the appliance having sliding rods, with one splint that can move with respect to the other by sliding of the lower rod inside the sleeve or by unscrewing of the upper rod inside the same sleeve. As will be described below, the wearer of the orthodontic appliance according to the invention simply has to insert or withdraw the single unit formed by the appliance and the splints and does not have to reinsert the male part of the appliance having sliding rods into the corresponding female part before each use.

The appliance having sliding rods will now be described in greater detail, based on FIGS. 3 and 4. As mentioned before, the appliance consists of two upper and lower rods and a sleeve inserted between the two rods.

The sleeve has an axial borehole from one end to the other with three different diameters, thus dividing the sleeve into three distinct functional portions, namely an adjustment portion 18 which corresponds to the smallest inside diameter and is designed to cooperate with the upper rod, a guide portion 19 which corresponds to the largest inside diameter and is designed to take the lower rod, and a central portion 20 which covers the distance between the two portions previously described.

From one end to the other, the inside of the sleeve comprises an end 21 designed to be folded inwards when the lower rod is inserted into the sleeve, a guide portion, a first shoulder 22, a central portion whose diameter is less than that of the guide portion, a second shoulder 23 and, finally, an adjustment portion, whose diameter is less than that of the central portion.

Part of the lower rod, including at least the collar and a spiral spring 24, slides into the guide portion. The diameter of the guide portion of the rod is such that it can take both the rod and the buffer spring.

The outside diameter of the collar in the guide portion is slightly less than the inside diameter of the sleeve so that the rod can slide easily and correctly into the sleeve. The first rod is kept inside the sleeve by a combination of the additional thickness of the collar and crimping of the end of the sleeve so that the collar and the guide portion of the lower rod remain imprisoned in the sleeve, with the lower rod being more or less pushed into the sleeve according to whether or not the intermediate portion is pushed into the sleeve.

The spring is thus trapped axially between the shoulder of the sleeve and the collar of the lower rod. It can be seen in FIG. 3, for example, that only axial displacement of the spring is permitted, so that lodging of the spring inside the sleeve forces the spring to be in compression or pure depression.

The adjustment portion receives part of the upper rod, that is, part of the threaded section of the rod.

The free end of the adjustment portion of the sleeve has a smaller inside diameter than the rest of the guide portion and it is the free end that has the internal thread designed to cooperate with the threaded portion of the upper rod. When the upper rod is screwed into the sleeve, the threaded portion cooperates with the internal thread at the end of the sleeve. After that, the wider inside diameter provides sufficient clearance for the rod to be gripped at the end of the sleeve only.

The sleeve has at least one radial hole 25 bored through the sleeve, designed to take a key that will allow the sleeve to rotate. Rotation of the sleeve causes screwing or unscrewing of the rod, depending on the resulting direction of rotation of the sleeve with respect to the lower rod which remains fixed with respect to the upper jaw to which it is attached.

Furthermore, as can be easily seen in FIG. 2, the end of the sleeve corresponding to the adjustment portion is split axially so as to form lugs 26 which receive the internal thread and are made so that they press down on the threaded rod, preventing it from being screwed or unscrewed as a result of inadvertent vibration on the part of the practitioner. The system is thus self-locking for precise, reliable adjustment of jaw alignment over the course of time, and, in conjunction with the radial holes, provides a means of adjusting the upper rod position with respect to the sleeve and therefore, by extension, that of the jaws.

Thus, by means of the adjustment system, that is, by self-locking rotation of the sleeve engaging with the upper rod, the alignment of the upper and lower jaws can be adjusted by screwing or unscrewing. Advantageously, four radial holes are bored at regular intervals through the sleeve as shown clearly in FIG. 2. The practitioner thus adjusts the appliance by rotating the sleeve using successive quarter turns in one direction or the other. The holes are arranged axially in the middle of the sleeve, in the central portion, but they could also be placed closer to the adjustment portion.

The central portion mainly serves as a clearance area for the upper and lower rods. In this case, the central portion must be long enough for each of the rods to be in their respective end positions shown in FIG. 4 without touching. It can be observed that, as a result of this design, the rods can be solid and not hollow inside so that they confer upon the appliance according to the invention a degree of resistance adapted to the stresses imposed by the jaws which tend to return to their initial position before treatment.

It can be understood from the above that the sleeve between the rods results in an orthodontic appliance having rods connecting occlusal splints associated with the jaws in which one rod cooperates with the sleeve to allow adjustment by screwing before use while the other rod cooperates with the sleeve by sliding when the appliance is in place, to allow the jaws to move during use.

The mounting and use of the orthodontic appliance having a sliding rod system according to a first construction method of the invention will now be described, based on FIGS. 1 to 4. This type of appliance is used to treat so-called class II malocclusion, where the mandible is retruded in relation to the maxilla, and sliding of the rods is aimed at posturing the mandible forwards and the maxilla backwards.

The lower rod and sleeve are first assembled. To do so, before crimping the end corresponding to the guide portion of the sleeve, the spring is inserted into the sleeve until it comes up against the shoulder that prevents it from moving any further, then the lower rod is inserted by sliding the guide portion of the rod through the spring. The lower rod is pushed as far inside the sleeve as possible until the compressed spring prevents it from going any further and the lower rod is held in this position with the collar of the rod inside the sleeve. The sleeve is then crimped to enclose the collar in the sleeve. Crimping is carried out such that the lower rod can slide without the intermediate portion being blocked by the part of the sleeve that is folded inwards.

The upper rod is then assembled with the upper occlusal splint after which the lower rod is assembled with the lower occlusal splint. As described previously, the upper rod is attached to the metal reinforcement of the upper splint by means of a pin with a ball that passes through the eye and into the tube welded to the metal reinforcement, while the lower rod is attached to the metal reinforcement of the lower splint by means of a pin with a ball passing through the eye and into the tube welded to the metal reinforcement.

Finally, the free end of the upper rod, which is threaded, is screwed into the sleeve.

The result is an orthodontic appliance forming a single unit that can be placed directly over the teeth so that the splints cover each jaw, as seen in FIG. 1.

Once the appliance has been inserted into the patient's mouth, the physician can adjust the jaw alignment by using the adjustment means. When treating class II malocclusion, the appliance is inserted with the rod totally screwed in and subsequently adjusted by unscrewing the rod. Once it has been adjusted, screwing is self-locked by the shape of the end of the sleeve gripped around the threaded rod, and the sleeve and upper rod form a subassembly. It is the sliding of the lower rod with respect to the sleeve that will allow the user to open and shut the jaws. The appliance according to the invention allows the adjustment proposed by the practitioner to be maintained over the course of time while allowing the jaws to open and shut.

The joints connecting the two jaws tend to force the jaws into their original position before the appliance was inserted.

In the case of a forward temporomandibular adjustment, that is, when the lower jaw is forced forwards with respect to the upper jaw, the joints tend to pull the lower jaw backwards, and therefore to slide the lower rod towards the inside of the sleeve (direction of arrow R, shown as an example in FIG. 4). The sliding movement of the rod with respect to the sleeve prevents it from brutally opposing the movement of the joints. The presence of the spring means that displacement is initially cushioned, after which it tends to pull the jaw into the advanced position determined by the practitioner.

The description above clearly explains how the invention is able to achieve its objectives. The invention allows for the displacement of one of the jaws with respect to the other, both in the sagittal and transverse directions. In the sagittal direction, the invention thus facilitates movement of the displaced jaw, whether backwards, as a result of the cushioning spring, or forwards, as a result of sliding of the lower rod inside the sleeve.

In the transverse direction, the S-shape or C-shape of the appliance rods allows the jaws to move sideways and for the mouth to be opened fully.

The invention also has the advantage of protecting the joints which naturally tend to oppose the forced displacement of the jaw, and it is particularly advantageous in this respect that the means used to adjust the spacing of the appliance according to the invention should allow carefully controlled adjustment of the jaw alignment by successive quarter turns, with no backward movement being possible due to self-locking.

It is advantageous that the structure of the sliding appliance in the invention should allow the upper rod to be screwed into the sleeve and the lower rod to slide inside the sleeve. Tests have shown that this arrangement offers the greatest freedom for taking into account the sideways movement of one jaw in relation to the other.

It is also advantageous for the spring to be lodged inside the sleeve. The spring is thus protected and is correctly guided to achieve straight compression, with the sleeve guiding the spring and the lower rod due to its rigidity.

The invention allows for adjustment by means of an appliance having sliding rods, to adjust the initial spacing of one rod with respect to the other. Although the rods do not separate completely, they can nevertheless offer sufficient functional play to allow the jaw to move sideways and the mouth to open and shut. It is particularly advantageous to have rods that do not separate completely because it makes the appliance easier to use. Once it is mounted, the appliance only requires a simple operation to insert and remove it from the mouth and wearers no longer have to connect up the rods themselves beforehand as they did in the past.

The invention is perfectly applicable to any type of orthodontic appliance, particularly retainers and active appliances, and to any type of use, such as the treatment of sleep apnoea.

Figure 5:
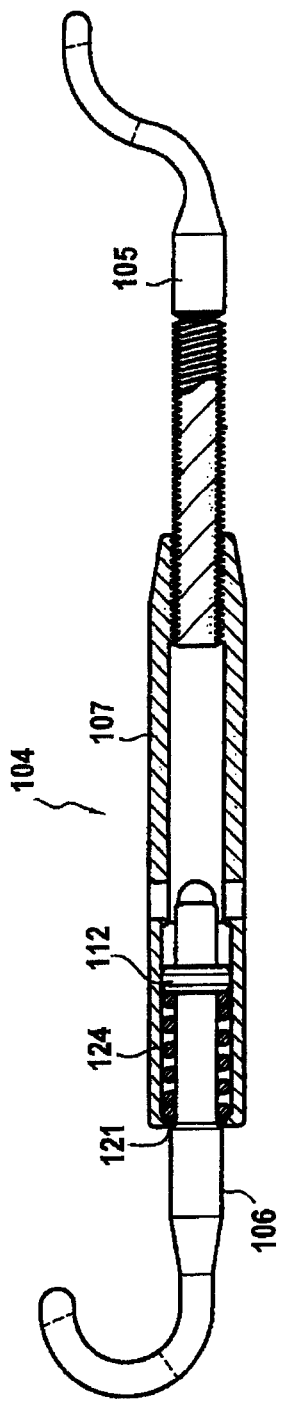
FIGS. 5 and 6, which are cross-sections of an appliance having sliding rods according to a variant of the invention, in similar positions to those illustrated in FIGS. 3 and 4 respectively.
Figure 6:
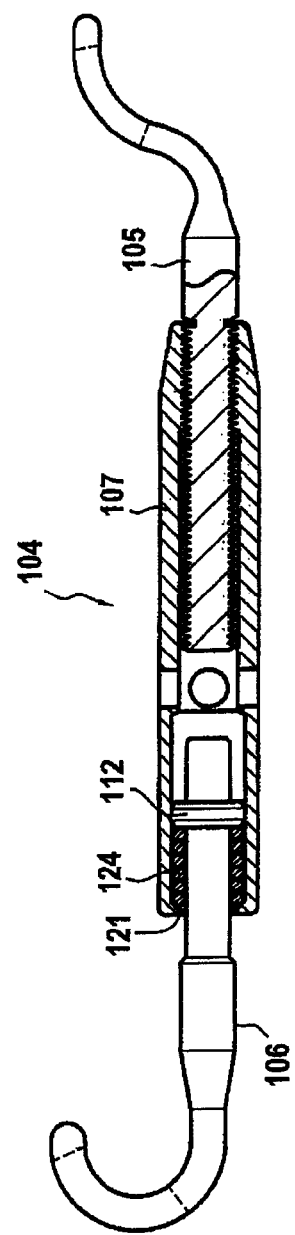

As an example, we are now going to describe a second embodiment, illustrated in FIGS. 5 and 6, in which the appliance is used for treatments that require the lower jaw to be postured towards the upper jaw. This type of appliance is used to treat so-called class III malocclusion, where the mandible is retruded in relation to the maxilla, and sliding of the rods is aimed at posturing the mandible forwards and the maxilla backwards. The same numerical references are used to indicate the same component of the appliance having sliding rods 4, with the addition of 100 each time.

The main result is that appliance 104 is inserted into the wearer's mouth with the upper rod 105 unscrewed in order to take up a maximum extended position (visible in FIG. 5). The practitioner uses adjustment means to rotate the sleeve 107 by quarter turns in order to gradually screw the upper rod into the sleeve and thus posture the upper jaw towards the lower jaw. The joint now tends to return to its initial position and stretch the appliance having sliding rods. Spring 124 lodged in the sleeve over the lower rod is now placed between the crimped end of sleeve 121 and the collar of rod 112 such that it is compressed when the lower rod is pulled (visible in FIG. 6), the spring tending to draw the lower rod back into its original position, this time towards the inside of the sleeve. As above, the use of a spring that provides cushioning is aimed at relieving pressure on the joints.

In the examples given, as represented in FIG. 1, the tube associated with the lower part of the appliance is welded to the metal reinforcement at the first lower premolars, while the tube associated with the upper part of the appliance is welded to the metal reinforcement at the upper molar. It is understood that this is only given as an example and that the position of the tubes can be different since the appliance having sliding rods enables one jaw to move with respect to the other.

However, the invention is not limited to the embodiments specifically described in this document and extends, in particular, to all equivalent means and any technically feasible combination of these means.

The invention claimed is:

1. An orthodontic appliance comprising:
   a first support positionable in a lower jaw region;
   a second support positionable in an upper jaw region;
   a first rod including a first end and a second end opposite the first end with the second end thereof being configured to be attached to the first support positionable in the lower jaw region;
   a second rod including a first end and a second end opposite the first end with the second end of the second rod being configured to be attached to the second support positionable in the upper jaw region and the first end of the second rod further comprising a threaded section,
   the first and second rods being solid and not hollow and configured to move in relation to each other; and
   a sleeve inserted between the first ends of the first and second rods, the first ends of the first and second rods configured to be held in the sleeve, such that the first ends of the first and second rods move relative to the sleeve between a first end adjustment position and a second end adjustment position, the first and second rods being closer to each other in the second end adjustment position,
      wherein the sleeve comprises (i) a spacing adjustment portion configured to thread together with the threaded section of the second rod at one end of the sleeve, (ii) a guide portion comprising a spring, the guide portion configured to allow the first rod to be slidably mounted inside the sleeve at an end of the sleeve opposite the one end having the spacing adjustment portion, and (iii) a central portion between the guide portion and the spacing adjustment portion, the first and second rods being configured to each have, in the second end adjustment position, the first end in the central portion in a non-touching arrangement, and
      wherein the sleeve further comprises a spacing adjustment mechanism configured to adjust the position of the second rod with respect to the sleeve by screwing and unscrewing.

2. The orthodontic appliance according to claim 1, wherein the sleeve is deformed at the end of the guide portion to form a retaining system configured to keep the first rod inside the sleeve.

3. The orthodontic appliance according to claim 1, wherein the adjustment mechanism comprises radial holes on a portion of a circumference of the sleeve, spaced at regular angular intervals, and configured to receive a key such that the sleeve can be rotated and correspondingly screwed or unscrewed with respect to the second rod.

4. The orthodontic appliance according to claim 1, wherein starting with the first end of the first rod configured to be held in the sleeve and ending with the second end of the first rod opposite the first end of the first rod, the first rod includes a guide portion of the rod that is approximately straight, then a collar that protrudes radially over the entire diameter of the first rod and separates the guide portion from the rest of the first rod, the first rod comprising an approximately straight intermediate portion, with a smaller diameter than a diameter of the collar and a greater diameter than the diameter of the guide portion, followed by an attachment portion which extends the intermediate portion in an approximate C-shape with an elongated hole or eye, the attachment portion configured to cooperate with the first support.

5. The orthodontic appliance according to claim 1, wherein starting at the first end of the second rod configured to thread with the sleeve and ending with the second end of the second rod opposite the first end of the second rod, the second rod includes a threaded end portion followed by an attachment portion, which extends the threaded end portion in an approximate S-shape with an elongated hole or eye, the attachment portion being configured to cooperate with the second support.

6. The orthodontic appliance according to claim 1, wherein the first and second rods are attached to the corresponding first and second support by a pin passing through an elongated hole or eye in the attachment portion of the first and second rods and through a tube welded to each of the first and second supports, the pin having a fine spindle configured to be inserted into the tube, and having a ball at an end thereof which abuts against the edges of the elongated hole or eye.

7. An orthodontic appliance comprising:
a first support positionable in a lower jaw region;
a second support positionable in an upper jaw region;
a first rod including a first end and a second end opposite the first end with the second end thereof being configured to be attached to the first support positionable in the lower jaw region;
a second rod including a first end and a second end opposite the first end with the second end of the second rod being configured to be attached to the second support positionable in the upper jaw region,
the first and second rods being solid and not hollow and configured to move in relation to each other; and
a sleeve inserted between the first ends of the first and second rods, the first ends of the first and second rods configured to be held in the sleeve, such that the first ends of the first and second rods move relative to the sleeve between a first end adjustment position and a second end adjustment position, the first and second rods being closer to each other in the second end adjustment position,
wherein the sleeve comprises (i) a spacing adjustment portion configured to thread together with a threaded section of the second rod at one end of the sleeve, (ii) a guide portion configured to allow the first rod to be slidably mounted inside the sleeve at an end of the sleeve opposite the one end having the spacing adjustment portion, and (iii) a central portion between the guide portion and the spacing adjustment portion, the first and second rods being configured to each have, in the second end adjustment position, the first end in the central portion in a non-touching arrangement,
wherein the sleeve further comprises a spacing adjustment mechanism configured to adjust the position of the second rod with respect to the sleeve by screwing and unscrewing,
wherein the sleeve comprises an axial boring which extends from the one end to the end of the sleeve opposite to the one end and has three portions of different internal diameter, dividing the sleeve into three distinct functional portions, and wherein the three distinct function portions include the spacing adjustment portion having a diameter configured to thread together with the second rod, the guide portion of a diameter larger than the diameter of the spacing adjustment portion and configured to allow the first rod to slide therein, and the central portion of an intermediate diameter between the diameter of the spacing adjustment portion and the diameter of the guide portion,
wherein the first rod has a collar that protrudes radially over a diameter approximately equal to an inside diameter of the guide portion of the sleeve and the end of the sleeve opposite to the one end, comprising the guide portion, folded inwards towards the first rod such that the collar is held inside the sleeve, and
wherein a spring is lodged inside the sleeve around the first rod configured to cooperate with the sleeve, and between the collar of the first rod and a shoulder formed inside the sleeve, such that the spring acts to draw the rod back into an initial position when displaced, the collar being configured to permit the spring the be lodged on one side or the other side of the collar.

8. An orthodontic appliance comprising:
a first support positionable in a lower jaw region;
a second support positionable in an upper jaw region;
a first rod including a first end and a second end opposite the first end with the second end thereof being configured to be attached to the first support positionable in the lower jaw region;
a second rod including a first end and a second end opposite the first end with the second end of the second rod being configured to be attached to the second support positionable in the upper jaw region,
the first and second rods being solid and not hollow and configured to move in relation to each other; and
a sleeve inserted between the first ends of the first and second rods, the first ends of the first and second rods configured to be held in the sleeve, such that the first ends of the first and second rods move relative to the sleeve between a first end adjustment position and a second end adjustment position, the first and second rods being closer to each other in the second end adjustment position,
wherein the sleeve comprises (i) a spacing adjustment portion configured to thread together with a threaded section of the second rod at one end of the sleeve, (ii) a guide portion configured to allow the first rod to be slidably mounted inside the sleeve at an end of the sleeve opposite the one end having the spacing adjustment portion, and (iii) a central portion between the guide portion and the spacing adjustment portion, the first and second rods being configured to each have, in the second end adjustment position, the first end in the central portion in a non-touching arrangement,
wherein the sleeve further comprises a spacing adjustment mechanism configured to adjust the position of the second rod with respect to the sleeve by screwing and unscrewing,
wherein the sleeve comprises an axial boring which extends from the one end to the end of the sleeve opposite the one end and has three portions of different internal diameter, dividing the sleeve into three distinct functional portions, and wherein the three distinct function portions include the spacing adjustment portion having a diameter configured to thread together with the second rod, the guide portion of diameter larger than the diameter of the spacing adjustment portion and configured to allow the first rod to slide therein, and the central portion of an intermediate diameter between the diameter of the spacing adjustment portion and the diameter of the guide portion, and wherein the spacing adjustment portion is split axially, forming lugs having an inside surface that is threaded to receive the second rod, the lugs being configured to press tightly against the second rod.

9. An orthodontic appliance comprising a first support positionable in a lower jaw region;

a second support positionable in an upper jaw region;

a first rod including a first end and a second end opposite to the first end, wherein the second end is attached to the first support;

a second rod including a first end and a second end opposite to the first end, wherein the second end is attached to the second support;

the first and the second rods being solid and not hollow and configured to move in relation to each other; and a sleeve inserted between the first ends of the first and second rods, wherein the first ends of the first and second rods are held in the sleeve such that the first ends of the first and second rods move relative to the sleeve between a first end adjustment position and a second end adjustment position, the first and the second rods being closer to each other in the second end adjustment position, wherein the sleeve comprises (i) a spacing adjustment portion configured to thread together with a threaded section of the second rod at one end of the sleeve, (ii) a guide portion configured to allow the first rod to be slidably mounted inside the sleeve at an end of the sleeve opposite the one end having the spacing adjustment portion, and (iii) a central portion between the guide portion and the spacing adjustment portion, wherein the first and second rods being configured to each have, in the second end adjustment position, the first end in the central portion in a non-touching arrangement, and wherein the sleeve further comprises a spacing adjustment mechanism configured to adjust the position of the second rod with respect to the sleeve by screwing and unscrewing;

wherein starting with the first end of the first rod held in the sleeve and ending with second end of the first rod opposite the first end of the first rod, the first rod includes a guide portion of the rod that is approximately straight, then a collar that protrudes radially over the entire diameter of the first rod and separates the guide portion from the rest of the first rod, the first rod comprising an approximately straight intermediate portion, with a smaller diameter than a diameter of the collar and a greater diameter than the diameter of the guide portion, followed by an attachment portion to the first support which extends the intermediate portion in an approximate C-shape with an elongated hole or eye through which a pin and a tube welded to the first support are passing, the pin having a fine spindle inserted into the tube, and having a ball at an end thereof which abuts against the edges of the hole or eye;

wherein starting at the first end of the second rod screwed into the sleeve and ending with the second end of the second rod opposite the first end of the second rod, the second rod includes of a threaded end portion followed by an attachment portion to the second support, which extends the threaded end portion in an approximate S-shape with an elongated hole or eye through which a pin and a tube welded to the second support are passing, the pin having a fine spindle inserted into the tube, and having a ball at an end thereof which abuts against the edges of the hole or eye.

* * * * *